United States Patent [19]

Greco et al.

[11] Patent Number: 4,948,888

[45] Date of Patent: Aug. 14, 1990

[54] PROCESS FOR THE PREPARATION OF STABILIZERS FOR ORGANIC POLYMERS

[75] Inventors: Alberto Greco, Milan; Luciano Pallini, Fornovo Taro, both of Italy

[73] Assignee: Enichem Sintesi S.p.A., Palermo, Italy

[21] Appl. No.: 80,259

[22] Filed: Jul. 27, 1987

Related U.S. Application Data

[63] Continuation of Ser. No. 791,410, Oct. 25, 1985, abandoned.

[30] Foreign Application Priority Data

Nov. 13, 1984 [IT] Italy ................................ 23539 A/84

[51] Int. Cl.$^5$ ............................. C07F 7/02; C07F 7/04
[52] U.S. Cl. ........................................ 544/69; 546/14; 548/406; 556/449; 556/469
[58] Field of Search .................. 556/449, 469; 546/14; 544/69; 548/406

[56] References Cited

U.S. PATENT DOCUMENTS

| | | | |
|---|---|---|---|
| 2,641,581 | 6/1953 | Fano | 556/469 X |
| 3,328,450 | 6/1967 | Plueddemann | 556/449 X |
| 4,374,742 | 2/1983 | Evans et al. | 556/449 X |

FOREIGN PATENT DOCUMENTS 1155602  5/1985  U.S.S.R. .

*Primary Examiner*—Richard L. Raymond
*Attorney, Agent, or Firm*—Hedman, Gibson, Costigan & Hoare

[57] ABSTRACT

Stabilizers for organic polymers are disclosed, of the type of sterically hindered phenols or amines, which are obtained by means of the reaction of a sterically hindered phenol or amine bearing in the molecule at least in alkoxysilanol group with a mono- or poly-hydroxy aliphatic alcohol, by a transesterification reaction.

The stabilizers so obtained are compatible with the organic polymers, wherein they remain stably.

9 Claims, No Drawings

PROCESS FOR THE PREPARATION OF STABILIZERS FOR ORGANIC POLYMERS

This is a continuation of application Ser. No. 791,410 filed Oct. 25, 1985, now abandoned.

The present invention relates to stabilizer compounds, of the type of sterically hindered phenols and amines, suitable to stabilize organic polymers. The invention relates also to the process for the preparation of said stabilizer compounds.

It is known that the organic polymers undergo degradation with time, due to the exposure to the environmental conditions, and that this degradation leads to a reduction of the physical properties of the polymers, such as e.g. of the ultimate tensile strength and of the flexibility, accompanied by a decrease of the viscosity index. To counteract such degradation it is usual in the art to introduce into the organic polymers small amounts of stabilizer compounds, generally constituted by sterically hindered phenols or amines.

The problems met in the stabilization of the organic polymers derive essentially from phenomena of incompatibility between the polymer and the stabilizer, and from phenomena of stabilizer release by the polymer. These phenomena are always occurring to a greater or smaller extent whenever the traditional stabilizer compounds are used, and the need has hence been felt of having available stabilizer compounds more compatible with the polymer, and capable of stably lasting within the same polymers. So, the U.S. Patent Applications Ser. No. 733526 and Ser. No. 733524 both filed on May 13, 1985 compounds have been disclosed of the type of phenols or amines, sterically hindered and bearing within their molecule a hydrolizable silicic function.

These compounds in the stabilization of the organic polymers are hydrolized at the silicic function and the silanol groups thus produced are able to interact with each other, or with a solid support, or with the organic polymer to be stabilized, in any case originating complex structures remaining stably within the organic polymer. It has been found now that said compounds, of phenolic or aminic structure, sterically hindered and bearing at least an alkoxysilanol group within the molecule, interact easily, by means of a transesterification reaction, with mono- and poly-hydroxy aliphatic alcohols, originating complex compounds which:

maintain unchanged their stabilizing characteristics deriving from the presence of the sterically hindered phenol or amino groups;
are easily dispersable into and homogenizable with the organic polymers, due to their oily or waxy character;
are completely compatible with said organic polymers;
show an exceptionally high thermal stability;
are not extracted from the organic polymers into which they are incorporated, not even under the most severe conditions.

Thus, according to the present invention, stabilizer compounds of the type of sterically hindered phenols or amines are prepared by means of the reaction of a phenol or of an amine sterically hindered and bearing at least one methoxysilanol or ethoxysilanol group within the molecule, with a mono-hydroxy aliphatic alcohol containing in its molecule at least 6 carbon atoms, or with a polyhydroxy alcohol bearing at least 4 carbon atoms in its molecule, with a ratio of the methoxy or ethoxy groups to the alcoholic hydroxy groups comprised within the range of from 1/1 to 3/1, by operating under transesterification conditions, in the presence of a transesterification catalyst and continuously removing the methanol or the ethanol which are formed as the by-products of the transesterification reaction, and recovering said transesterification product.

The sterically hindered phenols, useful to the purposes of the present invention, are those which can be defined by means of the following general formulae:

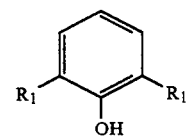

(I)

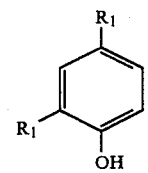

(II)

wherein the $R_1$ groups, equal to or different from each other, are alkyl radicals containing from 1 to 10 carbon atoms, preferably branched, and are tert.butyl radicals in the most preferred embodiment.

The sterically hindered amines, useful to the purposes of the present invention, are those which can be defined by means of the following general formulae:

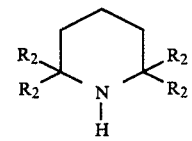

(III)

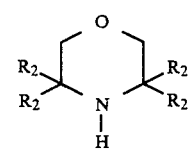

(IV)

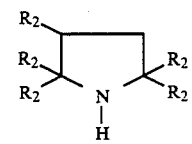

(V)

wherein $R_2$ are methyl radicals.

These sterically hindered phenols and amines contain within their molecule at least one methoxysilanol or ethoxysilanol group, i.e., one group which can be defined by means of the general formula:

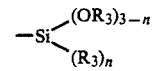

(Va)

wherein $R_3$ is the methyl or ethyl radical; and n is 0, 1 or 2.

Said group (va) is bonded to the sterically hindered phenol or amine through a silicon-carbon bond and in any possible position in the molecule of said phenol or amine.

Thus, typical classes of phenols or amine, sterically hindered and bearing at least one methoxy or ethoxysilanol group are the following:

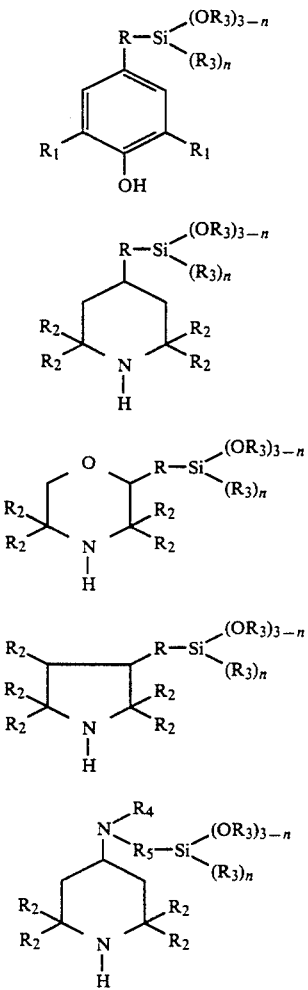

wherein R represents generally a straight or branched aliphatic hydrocarbon or oxy-hydrocarbon group containing from 2 to 10 carbon atoms, $R_4$ represents a straight or branched alkylene group, containing from 1 to 10 carbon atoms, and $R_5$ represents a straight or branched alkylene group, containing from 2 to 5 carbon atoms.

Specific examples of sterically hindered phenols or amines, containing methoxysilanol or ethoxysilanol groups are the following:

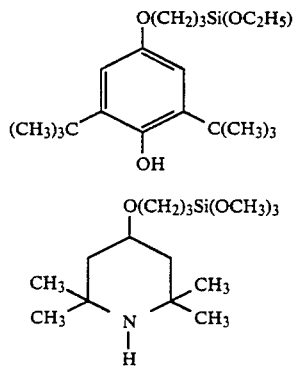

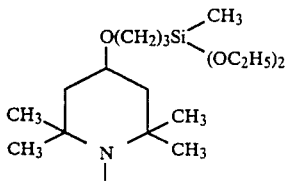

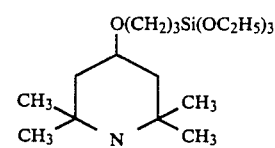

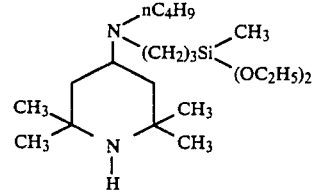

The sterically hindered phenol or amino compounds, bearing methoxysilanol or ethoxysilanol groups, can be prepared according to the general methods as disclosed in the hereinabove mentioned patent application, the disclosure of whose pertinent parts is herein incorporated by reference.

According to the present invention, the phenol or amino compounds sterically hindered and bearing methoxy- or ethoxysilanol groups are reacted, under transesterification conditions, with a mono-or poly-hydroxy aliphatic alcohol.

Alcohols suitable to the purpose are:
aliphatic monohydroxy alcohols containing from 6 to 18 carbon atoms, with straight or branched chain; such as hexanol, octanol, ethylhexanol, capryl alcohol, cetyl alcohol, lauryl alcohol and stearyl alcohol;
monoalkyl ethers of aliphatic dihydroxy alcohols, containing in the overall from 6 to 30 carbon atoms in their molecule; such as e.g., diethylene glycol monobutyl ether;
aliphatic dihydroxy alcohols or dihydroxy polyether alcohols containing from 4 to 12 carbon atoms, with straight or branched chain; such as butanediol, pentanediol, hexanediol, decanediol, 2,2-dimethylpropanediol and diethylene glycol;
aliphatic tri- or tetrahydroxy alcohols containing from 4 to 10 carbon atoms, such as pentaerythritol and trimethylolpropane.

According to the present invention, the reaction is carried out by reacting, in the absence of solvents or of diluents, the phenol or the amine sterically hindered and bearing methoxy- or ethoxy-silanol groups and the mono- or polyhydroxy alcohol, with a ratio of the methoxy or ethoxy groups to the alcoholic hydroxy of from 1:1 to 3:1, in the presence of a transesterification catalyst, and continuously removing the methanol or the ethanol which are formed as the reaction by-products.

Transesterification catalysts useful to the purpose are titanium alkoxides, magnesium alkoxytitanates, organic compounds of tin and of lead, such as dibutyltin oxide and lead octanoate, sodium silanates and alkaline metal alkoxides. Among all catalysts sodium methoxide is the preferred one, which may be conveniently used in an amount within the range of from 0.2 to 2% by weight relatively to the total weight of the reactants, and which may be fed as a solution in methanol.

The reaction temperatures are generally comprised with in the range of from 100° to 150° C. and the corresponding reaction times are from about 4 hours to about 30 minutes.

To the purpose of removing more easily the methanol and the ethanol which are formed as the reaction by-products, it is possible to operate under a reduced pressure and/or to make an inert gas such as nitrogen flow into the reaction mass.

At the end of the reaction it may be convenient to neutralize the catalyst and remove the catalyst residues. So, in the case of sodium methoxide, at the end of the reaction acetic acid can be added, and the so formed sodium acetate is removed by filtering.

The products of the transesterification reaction are more or less complex as a function of the number of methoxy or ethoxy groups and of the hydroxy groups bounded to the reactants. In this reaction it is not necessary that all the said functional groups are reacted. It is important instead that said reaction products reach molecular weights of at least 200 and preferably comprised within the range of from 300 to 1000.

Under these conditions, the desired stabilizer compounds are obtained as oils or waxes, colourless or slightly colored of pale yellow, which are completely soluble in the most common organic solvents, in particular in the aliphatic hydrocarbons, such as hexane, heptane and isooctane.

By means of the stabilizer compounds of the present invention, all organic polymers in general and in particular the homopolymers and copolymers of olefins, of diolefins, such as polypropylene, polybutadiene and polyethylene can be stabilized.

The incorporation of the stabilizer into the organic polymer and the homogenizing between the stabilizer and the polymer can be carried out by means of the usual techniques.

The stabilized polymeric compositions contain generally such an amount of stabilizer as to bring an amount of from 0.005 to 0.02% by weight of nitrogen in the case of the sterically hindered amines, and from 0.001 to 0.55% by weight of phenolic hydroxy function in the case of the sterically hindered phenols.

The following experimental examples are illustrative and not limitative of the invention.

EXAMPLES 1-10

In these experimental examples the following general procedure is used.

The reactants are introduced into a 25 ml flask under an atmosphere of anhydrous nitrogen. The flask is equipped with a magnetic-bar stirrer, with a nitrogen inlet pipe, and with a Liebig condenser. The flask is immersed into a bath heated at 120° C., and then sodium methoxide (as a 30% by weight solution in methanol) is added in an amount of 0.5% by weight relatively to the reactants.

The reaction is made proceed over two hours, at the temperature said, while flowing a weak nitrogen stream. At the end of the said time a vacuum of 50 torr is applied over the subsequent 20 minutes.

The process is then continued by cooling to the room temperature (20°-25° C.) and acetic acid (30 mg) is then added.

After one hour the excess acetic acid is removed by applying the vacuum (5 torr; 100° C.).

In order to obtain sodium acetate-free reaction products, said reaction products are dissolved in isooctane and the mass is then filtered through paper. The isooctane is then removed in vacuo (50 torr) from the filtrate.

To the purpose of measuring the amount of methanol or of ethanol developed during the reaction, the flask is weighed before the reaction and after the completion of the reaction.

The results relating to the Examples 1-10 are reported in the following Table.

TABLE

| Example | Compound A Type | Compound A Mmol | Compound B Type | Compound B Mmol | A/B Ratio | N (% by weight) | Developed alcohol (g) | Reaction yield (%) | Volatility $t^1$ | Volatility $t^2$ | Volatility $t^3$ | Molecular weight |
|---|---|---|---|---|---|---|---|---|---|---|---|---|
| 1 | I | 10.0 | OA | 20.0 | 2.0 | 2.7 | 22 | 100 | 255 | 280 | 300 | 485 (*) |
| 2 | I | 10.0 | SA | 10.0 | 1.0 | 2.5 | 10.3 | 100 | 260 | 315 | 360 | 505 (**) |
| 3 | I | 10.0 | CA | 10.0 | 1.0 | 2.6 | 10.3 | 100 | 250 | 300 | 340 | — |
| 4 | I | 10.0 | LA | 15.0 | 1.5 | 2.5 | 15.8 | 100 | 240 | 305 | 345 | — |
| 5 | II | 20.0 | HD | 20.0 | 1.0 | 3.5 | 21.9 | 55 | 315 | 355 | 395 | — |
| 6 | II | 10.0 | BD | 10.0 | 1.0 | 3.8 | 11.7 | 58 | 215 | 245 | 325 | — |
| 7 | II | 10.0 | PD | 10.0 | 1.0 | 3.6 | 10.2 | 51 | 355 | 370 | 390 | — |
| 8 | II | 9.7 | DEG | 9.7 | 1.0 | 3.6 | 10.0 | 52 | — | — | — | — |
| 9 | III | 10.0 | LA | 15 | 1.5 | 2.5 | 15.3 | 100 | 250 | 305 | 345 | — |
| 10 | IV | 5.0 | OA | 10.0 | 2.0 | — | 9.8 | 98 | 250 | 275 | 312 | 426 (*) |
| 11 | I | — | — | — | — | 4.39 | — | — | 140 | 155 | 180 | 319 |
| 12 | II | — | — | — | — | 4.23 | — | — | 145 | 165 | 190 | 331 |
| 13 | III | — | — | — | — | 3.88 | — | — | 160 | 170 | 190 | 361 |
| 14 | IV | — | — | — | — | — | — | — | 215 | 235 | 255 | — |

In this Table the A component is the sterically hindered phenol or amine, bearing methoxy- or ethoxysilanol groups. In particular, the following compounds have been used:

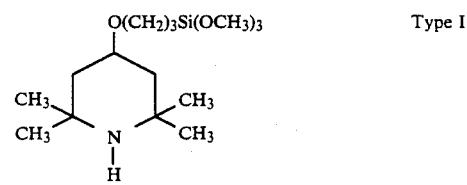

Type I

-continued

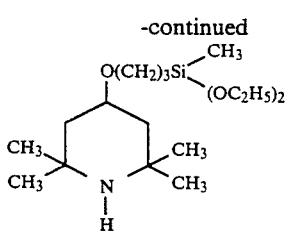
Type II

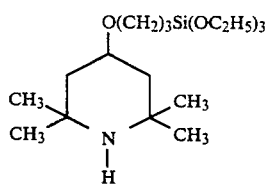
Type III

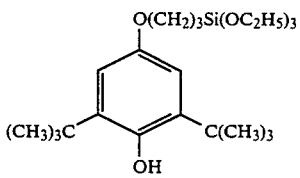
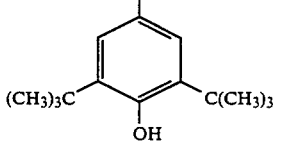
Type IV

In the Table, also the amount by moles of such compounds fed to the reaction is reported.

By "B Compound" the mono- or poly-hydroxy alcohol is meant, and in particular the following types of alcohols have been used:

| | |
|---|---|
| OA | 2-ethyl-1-hexanol |
| CA | cetyl alcohol |
| SA | stearyl alcohol |
| LA | lauryl alcohol |
| BP | 1,4-butanediol |
| PD | 1,5-pentanediol |
| HD | 1,6-hexanediol |
| DEG | diethylene glycol |

In the Table also the amount by moles of alcohol fed to the reaction is reported.

The other data reported in the Table are:
the molar ratio of the compound A to the compound B fed to the reaction;
the % by weight of nitrogen (as determined by means of the elemental analysis) in the case of aminic stabilizer compounds;
the amount in grams of methanol or of ethanol developed during the course of the transesterification, as determined by weighing as previously indicated;
the yield of the transesterification reaction, expressed as:
(mmoles of methanol or ethanol developed/mequivalents of OH hydroxy groups in the mono- or polyhydroxyalcohol)×100;
volatility of the product, as determined by thermogravimetric analysis (temperature increasing rate 10° C. per minute, transportation gas nitrogen at 10 l/hour); $t^1$, $t^2$ and $t^3$ correspond respectively to the temperatures (°C.) at which the reaction product loses ⅛, ¼ and ½ of its weight;
molecular weight of the reaction product, as determined by VPO (vapour phase osmometry) in methanol (*) or in toluene (**).

In the Table the volatility values of A compounds as such are reported (Examples 11, 12, 13 and 14).

The better values of thermal stability of the stabilizer compounds according to the present invention than of A compounds as such can be noted.

We claim:

1. A process for the preparation of stabilizer compounds comprising reacting a sterically hindered amine compound of the following formulae:

wherein R is selected from an aliphatic hydrocarbon and an oxyhydrocarbon group having 2 to 10 carbon atoms; $R_2$ is methyl; $R_3$ is selected from methyl and ethyl; $R_4$ is selected from a straight and branched chain alkyl group having from 1 to 10 carbon atoms; $R_5$ is selected from a straight and branched chain alkylene group having from 2 to 5 carbon atoms; and n is selected from 0, 1 and 2, with a monohydroxy aliphatic alcohol having at least 6 carbon atoms or a polyhydroxy aliphatic alcohol having at least 4 carbon atoms, wherein the ratio of the methoxy or ethoxy groups to the alcoholic hydroxy groups is within the range of 1/1 to 3/1, under transesterification conditions and in the presence of a transesterification catalyst whereby methanol or ethanol is formed as a by product, continuously removing said by-product from the transesterification reaction and recovering said stabilizer compounds from said transesterification reaction.

2. The process of claim 1, wherein the aliphatic mono- or polyhydroxyalcohol is selected from hexanol, octanol, ethylhexanol, caprylic alcohol, cetyl alcohol, lauryl alcohol, stearyl alcohol, diethylene glycol monobutyl ether, butanediol, pentanediol, hexanediol, decanediol, 2,2,-dimethylpropanediol, diethylene glycol, pentaerythritaol and trimethylolpropane.

3. The process of claim 1, wherein the transesterification catalyst is sodium methoxide which is present in an amount of from 0.2 to 2% by weight based on the weight of the reactants.

4. The process of claim 1, further comprising conducting the transesterification reaction in the absence of solvents or diluents at a temperature of from 100° to 150° C., under reduced pressure or under a flow of inert gas, or under reduced pressure and under a flow or inert gas, until the stabilizer compound recovered has a molecular weight of at least 200.

5. The process of claim 4, wherein the stabilizer compound has a molecular weight in the range of from 300 to 1000.

6. The process of claim 1, wherein the transesterification reaction is carried out for 20 minutes to 4 hours.

7. The process of claim 1 wherein the reaction temperature is from 100° C. to 150° C.

8. The process of claim 1 wherein said transesterification catalyst is neutralized catalyst residue is removed after the reaction is completed.

9. The process of claim 8 wherein said neutralizing agent is acetic acid and said transesterification catalyst residue is removed by filtration.

* * * * *

UNITED STATES PATENT AND TRADEMARK OFFICE
CERTIFICATE OF CORRECTION

PATENT NO. : 4,948,888

DATED : August 14, 1990

INVENTOR(S) : Alberto Greco et al.

It is certified that error appears in the above-identified patent and that said Letters Patent is hereby corrected as shown below:

Title page, Assignee should read

-- Enichem Synthesis S.p.A., Palermo, Italy --

Signed and Sealed this

Seventeenth Day of March, 1992

*Attest:*

HARRY F. MANBECK, JR.

*Attesting Officer*      *Commissioner of Patents and Trademarks*